US012727820B2

(12) United States Patent
Bauer

(10) Patent No.: US 12,727,820 B2
(45) Date of Patent: Sep. 8, 2026

(54) ELECTRODE FOR A GARMENT, A BELT OR A BANDAGE

(71) Applicant: NTT NEW TEXTILE TECHNOLOGIES GMBH, Balingen (DE)

(72) Inventor: Hans Bauer, Balingen (DE)

(73) Assignee: NTT NEW TEXTILE TECHNOLOGIES GMBH, Balingen (DE)

( * ) Notice: Subject to any disclaimer, the term of this patent is extended or adjusted under 35 U.S.C. 154(b) by 257 days.

(21) Appl. No.: 18/542,635

(22) Filed: Dec. 16, 2023

(65) Prior Publication Data

US 2024/0148325 A1 May 9, 2024

Related U.S. Application Data

(63) Continuation-in-part of application No. PCT/EP2023/025172, filed on Apr. 12, 2023.

(30) Foreign Application Priority Data

Apr. 29, 2022 (DE) ..................... 10 2022 110 523.7

(51) Int. Cl.
*A61B 5/00* (2006.01)

(52) U.S. Cl.
CPC .... *A61B 5/6804* (2013.01); *A61B 2560/0468* (2013.01); *A61B 2562/02* (2013.01); *A61B 2562/14* (2013.01); *A61B 2562/164* (2013.01); *A61B 2562/227* (2013.01)

(58) Field of Classification Search
None
See application file for complete search history.

(56) References Cited

U.S. PATENT DOCUMENTS

2006/0183990 A1 8/2006 Tolvanen
2008/0091097 A1 4/2008 Linti et al.
2009/0043185 A1* 2/2009 McAdams ........... A61N 1/0492 600/372
2014/0135593 A1* 5/2014 Jayalth ............... G09B 19/0038 600/301
2016/0228691 A1* 8/2016 Mathew ............... A61N 1/0496
2020/0046246 A1 2/2020 Shu et al.

(Continued)

FOREIGN PATENT DOCUMENTS

CN 107951484 A 4/2018
DE 10 2008 042 654 A1 4/2010
DE 20 2014 104 995 U1 5/2015

(Continued)

OTHER PUBLICATIONS 2021 (Year: 2021) Smart Garment Having a Contact Electrode , Wohnsdorf Silke ( Translation).*

(Continued)

*Primary Examiner* — Mallika D Fairchild
(74) *Attorney, Agent, or Firm* — Ronald S. Lombard

(57) ABSTRACT

An electrode for a garment comprises several superimposed layers, wherein one layer is an electrically conductive electrode layer and another layer is a foamed material layer, wherein an electric conductor extends between the electrode layer and the foamed material layer and is in contact with the electrode layer.

10 Claims, 1 Drawing Sheet

(56) References Cited

U.S. PATENT DOCUMENTS

2021/0007223 A1 1/2021 Kwon et al.
2023/0031279 A1 2/2023 Chahine et al.

FOREIGN PATENT DOCUMENTS

DE 20 2018 100 556 U1 3/2018
JP 2014 028 180 A 2/2014
WO WO 2020/186975 A1 10/2020
WO WO-2021110711 A1 * 6/2021 ............. A41D 1/005
WO WO-2022061250 A2 * 3/2022 ........... A61B 5/6804

OTHER PUBLICATIONS

International Search Report in the German language for the corresponding international application No. PCT/EP2023/025172; dated Jul. 19, 2022; 3 pages.
English translation of the International Search Report for the corresponding International cation No. PCT/EP2023/025172; dated Jun. 23, 2023; 2 pages.
German Patent Office Search Report In the German language for the corresponding priority German patent application No. 10 2022 110 523.7; dated Dec. 1, 2022; 12 pages.

* cited by examiner

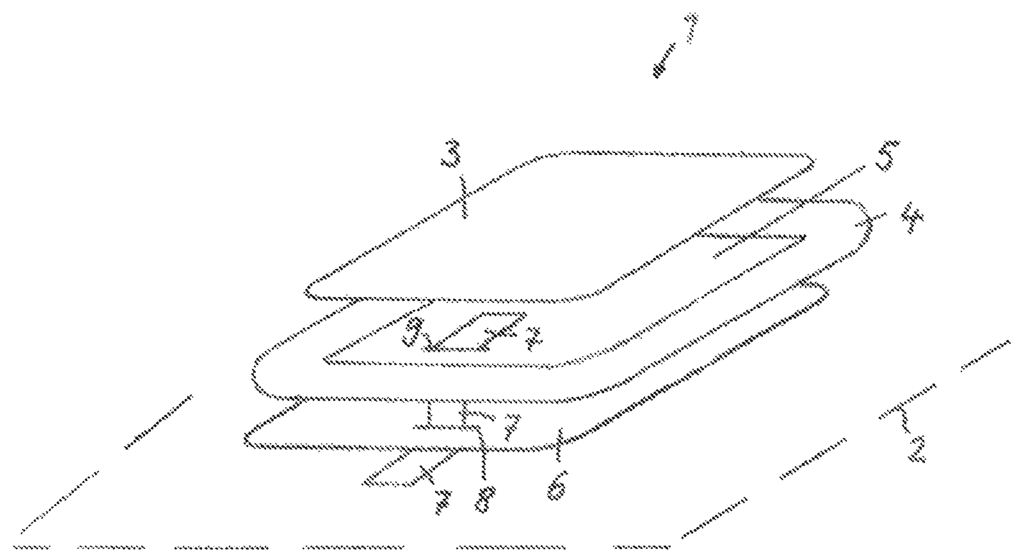
1
3
5
4
9
7
7
2
7
8
6

ELECTRODE FOR A GARMENT, A BELT OR A BANDAGE

CROSS-REFERENCE TO RELATED APPLICATIONS

This is a continuation-in-part application of pending international patent application PCT/EP2023/025172 filed Apr. 12, 2023 and claiming the priority of German patent application No. 10 2022 110 523.7 filed Apr. 29, 2022. Both the said international patent application PCT/EP2023/025172 and the said German patent application No. 10 2022 110 523.7 are incorporated herein by reference in their entireties as though fully set forth.

BACKGROUND OF THE INVENTION

The invention relates to an electrode for a garment, a belt, or a bandage. Furthermore, the invention relates to a fabric layer-electrode combination with an electrode and to a garment, a belt or a bandage with a fabric layer-electrode combination, wherein the electrode is connected to a fabric layer of the garment, the belt or the bandage.

Electrodes in the form of expansion sensors which are disposed on a fabric layer in order to monitor the expansion of the fabric layer are known. DE 10 2008 042 554 A1 for example describes an elastic chest belt for monitoring the breathing of a patient wherein an expansion sensor is disposed on the chest belt and connected to an evaluation unit on the chest belt.

JP 2014 025 180 A discloses a pants with an integrated expansion sensor which is connected to the fabric of the pants by an elastic adhesive. By the expansion sensor expansion of the material of the pants can be detected. The sensor signals are transmitted to an external apparatus by a transmitter which is also integrated into the pants.

CN 107 951 484 discloses a multi-layer electrode for a piece of clothing with an electrically conductive contact layer and an underlying conductor plate wherein between the contact layer and the conductor plate an isolating foam material layer is disposed. The contact layer is electrically connected to the conductor plate by way of a conductor which extends through the foam material layer.

WO 2022/061250 A2 also discloses a multi-layer electrode which includes an upper electrically conductive layer, and disposed underneath, a polyethylene film, a resilient support layer and, at the bottom, a rubber layer. The electrically conductive layer may be a conductive fabric layer or a conductive silicon layer.

Concerning additional state of the art, reference is made to US 2020/0046246 A1 and DE 20 2014 104 995 U1.

It is the object of the present invention to provide, with simple measures, a secure electrical connection between an electrode and an electrical connector.

SUMMARY OF THE INVENTION

The object is achieved by the features of the independent claims. The dependent claims are concerned with further developments.

The electrode according to the invention with an electrical conductor may be used for example for underwear or, possibly, upper wear clothing, for example for a T-shirt or a sport pants. Also possible is its use for a bandage, in particular a joint bandage for example a knee bandage or an elbow bandage or a body belt. A fabric layer with which the electrode may be interconnected may be part of the garment, the belt or, respectively, the bandage or the fabric layer may be connected to the garment, the belt or the bandage.

The electrode consists of several superimposed layers which extend in parallel planes. One layer is an electrically conductive electrode layer and another layer is a foamed material layer which is connected directly or indirectly to the electrode layer. An electrical conductor extends between the electrode layers and the foam material layer and is in physical and electrical contact with the electrode layer. Electric impulses can be transmitted via the electric conductor to an evaluation unit measuring for example vital parameters such as heart pulse frequency or the skins electrical resistance. It is also possible to transmit electrical impulses via the electrical conductor to the electrode layer for stimulation. The electrode layer is in direct contact with the skin of the wearer during wearing of the garment or belt or bandage.

Providing the electrode with the foam material layer has the advantage that the wearing comfort is improved. The foam material layer stabilizes the electrode and keeps the electrode layer in shape so that an areal contact between the electrode layer and the skin of the wearer and, as a result, a good pulse transmission is ensured. The foam material layer is capable of absorbing humidity so that, on one hand, excess humidity is absorbed from the skin and, on the other hand, the electrical contact with the conductor, which is disposed between the foam material layer and the electrode layer is improved.

The electrode layer is in the form of a fabric layer which is provided with an electrically conductive elastomer. The elastomer is for example silicon and may contain electrically conductive particles for example silver or carbon particles or fibers.

In an advantageous embodiment the electrical conductor passes through a cavity in the foam material layer so that an end section of the electrical conductor extends parallel to the electrode layer providing for a relatively large contact area between the conductor and the electrode layer. The passing of the electrical conductor through the cavity in the foam material layer has the advantage that the electrical conductor does not extend over the side edge of the electrode layer but reaches the electrode layer from below through the foam material layer in a space-saving manner. Alternatively, embodiments are possible wherein the electrical conductor extends around the side wall of the electrode layer which has the advantage that the electric conductor does not need to be bent over.

The electrical conductor is for example in the form of a flexible electrically conductive fabric ribbon which can be bent-over one or several times. The electrically conductive fabric ribbon is for example a fabric ribbon which includes electrically conductive fibers or electrically conductive particles.

Between the electrical conductor layer and the foam material layer there is a fabric layer on which the electrode layer is supported. An end section of the electric conductor is disposed between the fabric layer and the electrode layer and, consequently is in contact with the electrode layer. The fabric layer may have an opening through which the electric conductor extends. The fabric layer has preferably a lower porosity than the foam material layer. Humidity such as perspiration is first absorbed by the fabric layer before it reaches the foam material layer so that the foam material layer remains essentially dry even during an extended use of the electrode. The fabric layer may be electrically conductive or it may be electrically insulating.

In a still further advantageous embodiment, at least one layer of the electrode is provided with a thermo adhesive foil via which a firm connection with an adjacent layer is established. Upon heating, material of the thermo adhesive foil enters the adjacent layer; upon curing the desired firm connection with the adjacent layer is established.

It may be expedient if the electrode layer as well as the foam material layer are provided with a thermo adhesive foil. On the electrode layer there is the thermo adhesive foil provided on the side facing the foam material layer in order to establish a connection with the facing layer which may be the foam material layer or, in a preferred embodiment, the fabric layer. The fabric layer may also have a thermo adhesive layer for connection with the foam material layer. The thermo adhesive foil on the foam material layer is advantageously provided on the side facing away from the electrode layer and serves for a connection with a fabric layer of the garment, the bandage or the belt.

In a further embodiment, the foam material layer is thicker than the electrode layer. This has the advantage to provide for a high stability of the electrode and, at the same time, for a high wear comfort.

The thickness of the foam material may be varied in a wide range depending on the particular requirements. The thickness is for example 1 mm or less or has a value of 20 mm or even more than 20 mm.

The foam material layer extends over a larger area than the electrode layer. The foam material layer extends beyond the electrode layer edges so that during wearing the projecting edge area is in contact directly with the skin whereby the comfort is improved.

The electrode layer may have a length of 100 mm or more than 100 mm.

As material of the foam layer open-cell foam material, for example polyurethane foam or polyester foam material may be used. Also closed cell foam material such as sponge rubber, neopolene, polyethylene or cell rubber may be considered. Furthermore, mixed cell foam material in particular hybrid foam material of open-cell and closed-cell materials may be used. Furthermore, integral foam materials may be used such as silicon foam, polyester cold foam/HR foams (high-resistant) or latex foam materials may be used. Furthermore, foam materials may be used which consist only of one material or foam materials which consist of several materials that is for example mixtures with fabric or other materials. Furthermore, different types of foam material configurations may be used such as knup foam material.

Depending on the material used for the different layers, the electrode may be elastic or partially elastic or non-elastic in particular in a direction orthogonal to the plane of the layers of the electrode.

For the thermo adhesive foils used herein materials such as polyurethane, polyamide, polyester or thermoplastic elastomers may be considered. The thickness of the thermo adhesive foils is for example in a range of 10 micrometers to more than 500 micrometers.

It may further be expedient to apply to the outside of the electrode, in particular the electrode layer with elastomer, especially silicon, lettering or a logo preferably using a template or a nozzle. The elastomer may have a coloring substance or visible particles to improve visibility of the logo or letters.

Further advantages are apparent from the claims and the following description of advantageous embodiments of the invention with reference to the sole figure of the accompanying drawing.

BRIEF DESCRIPTION OF THE DRAWING

The sole FIGURE shows a perspective view of an electrode which includes several layers and is suitable for use on a fabric layer that is for example part of a garment, a bandage or a belt.

DETAILED DESCRIPTION OF THE INVENTION

The sole FIGURE shows the layered assembly of an electrode 1 including several parallel layers. The electrode 1 may be used as a sensor in a fabric layer 2 for example for determining vital parameters or for determining the expansion of the fabric layer 2, but also for muscle stimulation. The fabric layer 2 is part of a garment, a bandage or belt worn next to the body.

The electrode 1 comprises an electrode layer 3 in the form of an electrically conductive fabric layer, in particular a fabric layer and an electrically conductive elastomer, preferably silicon. The electrode 1 includes further a foam material layer 4 and a fabric layer 5 disposed between the electrode layer 3 and the foam material layer 4. At the bottom side of the foam material layer 4 there is a thermo adhesive foil 6 which, upon heating and subsequent cooling, is firmly connected to the fabric layer 2 on which the electrode 1 is disposed. A thermo adhesive foil may also be disposed on the bottom side of the electrode layer 3 for connection with the fabric layer 5 and also at the bottom side of the fabric layer 5 for connection with the foam material layer 4.

The foam material layer 4 is thicker than the electrode layer 3. The foam material layer 4 also covers a larger area than the electrode layer 3 so that the foam material layer extends over the edges of the electrode layer 3 and its edge areas abut directly the skin of the wearer for an improved comfort.

For an electrical contact of the electrode layer 3 the electrode 1 is provided with an electrical conductor 7 in the form of an electrically conductive fabric ribbon. Via the conductor 7 electrical impulses which are generated in the electrode layer 3 are transmitted to an evaluation unit. Vice versa it is also possible to transmit electrical pulses for skin or muscle stimulation from a pulse generating unit to the electrode layer 3.

The ribbon-like electrical conductor 7 extends through openings 8, 9 which are provided in the thermo adhesive foil 6 and in the fabric layer 5, respectively, in the form of slots. Also a thermo adhesive foil at the bottom side of the foam material layer 4 is provided with a corresponding slot-like opening for the electrical conductor 7, not shown in the sole FIGURE. In a thermo adhesive foil at the bottom side of the electrode layer 3, not shown in the sole FIGURE, there is expediently a layer-free area corresponding to the end section of the electrical conductor 7 adjacent the bottom side of the electrode layer 3, so that a direct contact between the electrode layer 3 and the electrical conductor is ensured.

LISTING OF REFERENCE NUMERALS

1 electrode
2 fabric material
3 electrode layer
4 foam material layer
5 fabric layer
6 thermo adhesive foil
7 electric conductor/fabric ribbon
8 opening
9 opening

What is claimed is:

1. An electrode (1) for a garment, a belt or a bandage, said electrode (1) comprising several superimposed layers including one layer in the form of an electrically conductive electrode layer (3) and another layer in the form of a foam material layer (4), wherein during wearing of the garment, the belt or the bandage, provided with the electrode (1), the electrode layer (3) is in direct contact with the skin of a wearer, wherein an electrical conductor (7) extends between the electrode layer (3) and the foam material layer (4) and is in contact with the electrode layer (3), characterized in that:

the electrode layer (3) includes a fabric layer and an electrically conductive elastomer disposed on or in the fabric layer, that between the electrode layer (3) and the foam material layer (4), there is a fabric layer (5) on which the electrode layer (3) is supported and that the foam material layer (4) extends over a larger area than the electrode layer (3), the electrical conductor (7) extends through an opening (9) in the foam material layer (4), the electrical conductor (7) configured as a ribbon-like device, and, a first end section of the ribbon-like electrical conductor (7) proximate the electrode layer (3) extends parallel to the electrode layer (3) without extending over a side edge of the electrode layer (3) and the first end section of the ribbon-like electrical conductor (7) configured for providing a relatively large contact area between the ribbon-like electrical conductor (7) and the electrode layer (3).

2. The electrode (1) according to claim 1, characterized in that the ribbon-like electrical conductor (7) extends through an opening (9) in the fabric layer (5).

3. The electrode (1) according to claim 1, characterized in that the ribbon-like electrical conductor (7) is in the form of a flexible electrically conductive fabric ribbon.

4. The electrode (1) according to claim 1, characterized in that at least one layer of the electrode (1) is provided with a thermo adhesive foil (6) for a connection with an adjacent layer.

5. The electrode (1) according to claim 1, characterized in that the foam material layer (4) is thicker than the electrode layer (3).

6. A fabric layer-electrode combination with an electrode (1) according to claim 1, wherein the electrode (1) is connected to a fabric layer (2) of a garment, a belt or a bandage.

7. A garment, belt or bandage with a fabric layer-electrode combination according to claim 6.

8. The electrode (1) according to claim 1, characterized in that the fabric layer (5) has a lower porosity than the foam material layer (4).

9. The electrode (1) according to claim 1, characterized in that the foam material layer (4) extends beyond edges of the electrode layer (3), wherein comfort of the wearer is improved.

10. The electrode (1) according to claim 4, characterized in that the ribbon-like electrical conductor (7) extends through an opening (8) in the thermo adhesive foil (6).

* * * * *